(12) United States Patent
Muller et al.

(10) Patent No.: US 8,177,778 B2
(45) Date of Patent: May 15, 2012

(54) SYSTEM AND METHOD FOR STABILIZING CORNEAL TISSUE AFTER TREATMENT

(75) Inventors: David Muller, Boston, MA (US); John Marshall, Farnborough (GB)

(73) Assignee: Avedro, Inc., Waltham, MA (US)

( * ) Notice: Subject to any disclaimer, the term of this patent is extended or adjusted under 35 U.S.C. 154(b) by 0 days.

(21) Appl. No.: 12/915,646

(22) Filed: Oct. 29, 2010

(65) Prior Publication Data

US 2011/0118716 A1 May 19, 2011

Related U.S. Application Data

(60) Provisional application No. 61/256,714, filed on Oct. 30, 2009.

(51) Int. Cl.
*A61B 18/02* (2006.01)
(52) U.S. Cl. .................. 606/20; 606/21; 606/41
(58) Field of Classification Search .............. 606/20–52; 600/383; 514/241
See application file for complete search history.

(56) References Cited

U.S. PATENT DOCUMENTS

| | | | |
|---|---|---|---|
| 3,776,230 | A | 12/1973 | Neefe |
| 4,326,529 | A | 4/1982 | Doss et al. |
| 4,381,007 | A | 4/1983 | Doss |
| 4,490,022 | A | 12/1984 | Reynolds |
| 4,712,543 | A | 12/1987 | Baron |
| 4,743,725 | A | 5/1988 | Risman |
| 4,796,623 | A | 1/1989 | Krasner et al. |
| 4,805,616 | A | 2/1989 | Pao |
| 4,881,543 | A | 11/1989 | Trembly et al. |
| 4,891,043 | A | 1/1990 | Zeimer et al. |
| 4,994,058 | A | 2/1991 | Raven et al. |
| 5,103,005 | A | 4/1992 | Gyure et al. |
| 5,171,254 | A | 12/1992 | Sher |
| 5,281,211 | A | 1/1994 | Parel et al. |
| 5,332,802 | A | 7/1994 | Kelman et al. |
| 5,370,644 | A | 12/1994 | Langberg |
| 5,437,658 | A | 8/1995 | Muller et al. |
| 5,461,212 | A | 10/1995 | Seiler et al. |
| 5,490,849 | A | 2/1996 | Smith |
| 5,586,134 | A | 12/1996 | Das et al. |

(Continued)

FOREIGN PATENT DOCUMENTS

EP 1 561 440 8/2005

(Continued)

OTHER PUBLICATIONS

Search Report corresponding to International Patent Application Serial No. PCT/US2010/054673, United States Patent Office; dated Aug. 2, 2011 (4 pages).

(Continued)

*Primary Examiner* — Linda Dvorak
*Assistant Examiner* — Amanda Scott
(74) *Attorney, Agent, or Firm* — Nixon Peabody LLP

(57) ABSTRACT

Systems and methods stabilize corneal tissue after treatment of the corneal tissue. For example, thermokeratoplasty may be applied to the corneal tissue to address disorders associated with abnormal shaping of the cornea. To stabilize the desired structural changes caused by the treatment, embodiments apply ophthalmic formulations that help to inhibit wound healing. Wound healing may occur in response to the application of the treatment and may produce further structural changes that mitigate or alter the desired effects of the treatment.

6 Claims, 4 Drawing Sheets

U.S. PATENT DOCUMENTS

| | | |
|---|---|---|
| 5,618,284 A | 4/1997 | Sand |
| 5,624,456 A | 4/1997 | Hellenkamp |
| 5,634,921 A | 6/1997 | Hood et al. |
| 5,658,278 A | 8/1997 | Imran et al. |
| 5,766,171 A | 6/1998 | Silvestrini |
| 5,779,696 A | 7/1998 | Berry et al. |
| 5,814,040 A | 9/1998 | Nelson et al. |
| 5,830,139 A | 11/1998 | Abreu |
| 5,873,901 A | 2/1999 | Wu et al. |
| 5,885,275 A | 3/1999 | Muller |
| 5,910,110 A | 6/1999 | Bastable |
| 5,919,222 A | 7/1999 | Hjelle et al. |
| 6,033,396 A | 3/2000 | Huang et al. |
| 6,053,909 A | 4/2000 | Shadduck |
| 6,101,411 A * | 8/2000 | Newsome ............ 604/20 |
| 6,104,959 A | 8/2000 | Spertell |
| 6,139,876 A | 10/2000 | Kolta |
| 6,149,646 A | 11/2000 | West, Jr. et al. |
| 6,161,544 A | 12/2000 | DeVore et al. |
| 6,162,210 A | 12/2000 | Shadduck |
| 6,293,938 B1 | 9/2001 | Muller et al. |
| 6,319,273 B1 | 11/2001 | Chen et al. |
| 6,325,792 B1 | 12/2001 | Swinger et al. |
| 6,334,074 B1 * | 12/2001 | Spertell ............ 607/101 |
| 6,342,053 B1 | 1/2002 | Berry |
| 6,402,739 B1 | 6/2002 | Neev |
| 6,413,255 B1 | 7/2002 | Stern |
| 6,520,956 B1 | 2/2003 | Huang |
| 6,617,963 B1 | 9/2003 | Watters et al. |
| 6,749,604 B1 | 6/2004 | Eggers et al. |
| 6,946,440 B1 | 9/2005 | DeWoolfson |
| 7,044,945 B2 | 5/2006 | Sand |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,402,562 B2 | 7/2008 | DeWoolfson |
| 7,713,268 B2 | 5/2010 | Trembly |
| 2002/0002369 A1 | 1/2002 | Hood |
| 2002/0013579 A1 | 1/2002 | Silvestrini |
| 2002/0049437 A1 | 4/2002 | Silvestrini |
| 2002/0077699 A1 | 6/2002 | Olivieri et al. |
| 2002/0099363 A1 | 7/2002 | Woodward et al. |
| 2002/0164379 A1 | 11/2002 | Nishihara et al. |
| 2003/0018255 A1 | 1/2003 | Martin et al. |
| 2003/0097130 A1 | 5/2003 | Muller et al. |
| 2003/0175259 A1 | 9/2003 | Karageozian |
| 2003/0216728 A1 | 11/2003 | Stern et al. |
| 2004/0001821 A1 | 1/2004 | Silver et al. |
| 2004/0111086 A1 | 6/2004 | Trembly |
| 2004/0143250 A1 | 7/2004 | Trembly |
| 2004/0199158 A1 * | 10/2004 | Hood et al. ............ 606/41 |
| 2004/0243160 A1 | 12/2004 | Shiuey et al. |
| 2005/0033202 A1 | 2/2005 | Chow et al. |
| 2005/0070977 A1 | 3/2005 | Molina |
| 2005/0197657 A1 | 9/2005 | Goth et al. |
| 2005/0287217 A1 | 12/2005 | Levin et al. |
| 2006/0135957 A1 | 6/2006 | Panescu |
| 2006/0149343 A1 | 7/2006 | Altshuler et al. |
| 2006/0189964 A1 | 8/2006 | Anderson et al. |
| 2006/0206110 A1 | 9/2006 | Knowlton et al. |
| 2006/0254851 A1 | 11/2006 | Karamuk |
| 2006/0287662 A1 | 12/2006 | Berry et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0114946 A1 | 5/2007 | Goetze et al. |
| 2007/0123845 A1 | 5/2007 | Lubatschowski |
| 2007/0161976 A1 | 7/2007 | Trembly |
| 2007/0179564 A1 | 8/2007 | Harold |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2008/0015660 A1 | 1/2008 | Herekar |
| 2008/0027328 A1 | 1/2008 | Klopotek et al. |
| 2009/0024117 A1 | 1/2009 | Muller |
| 2009/0054879 A1 | 2/2009 | Berry |
| 2009/0069798 A1 | 3/2009 | Muller et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0187173 A1 | 7/2009 | Muller |
| 2009/0209954 A1 * | 8/2009 | Muller et al. ............ 606/33 |
| 2010/0094197 A1 | 4/2010 | Marshall et al. |

FOREIGN PATENT DOCUMENTS

| | | |
|---|---|---|
| EP | 1 790 383 | 5/2007 |
| EP | 2 269 531 | 1/2011 |
| WO | WO 99/17690 | 4/1999 |
| WO | WO 00/09027 | 2/2000 |
| WO | 0074648 A2 | 12/2000 |
| WO | WO 2004/052223 | 6/2004 |
| WO | 2006128038 A2 | 11/2006 |
| WO | WO 2007/022993 | 3/2007 |
| WO | 2007/120457 A2 | 10/2007 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Written Opinion corresponding to International Patent Application Serial No. PCT/US2010/054673, United States Patent Office; dated Aug. 2, 2011 (5 pages).

Corbett et al, "Effect of Collagenase Inhibitors on Coreal Haze after PRK", Exp. Eye Res., vol. 72, Issue 3, pp. 253-259, dated Jan. 29, 2001 (7 pages).

Alió, JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).

Alió, JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).

Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).

Andreassen TT, Simonsen AH, Oxlund H, "Biomechanical Properties of Keratoconus and Normal Corneas," *Experimental Eye Research*, vol. 31, Oct. 1980, pp. 435-441 (7 pages).

Anschutz T, "Laser Correction of Hyperopia and Presbyopia," *International Ophthalmology Clinics*, vol. 34, No. 4, Fall 1994, pp. 107-137 (33 pages).

Bailey MD, Zadnik K, "Outcomes of LASIK for Myopia With FDA-Approved Lasers," *Cornea*, vol. 26, No. 3, Apr. 2007, pp. 246-254 (9 pages).

Borja D, Manns F, Lamar P, Rosen A, Fernandez V, Parel JM, "Preparation and Hydration Control of Corneal Tissue Strips for Experimental Use," *Cornea*, vol. 23, No. 1, Jan. 2004, pp. 61-66 (7 pages).

Bower KS, Weichel ED, Kim TJ, "Overview of Refractive Surgery," *Am Fam Physician*, vol. 64, No. 7, Oct. 2001, pp. 1183-1190 (8 pages).

Braun EH, Lee J, Steinert RF, "Monovision in LASIK," *Ophthalmology*, vol. 115, No. 7, Jul. 2008, pp. 1196-1202 (7 pages).

Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).

Bryant MR, McDonnell PJ, "Constitutive Laws for Biomechanical Modeling of Refractive Surgery," *Journal of Biomechanical Engineering*, vol. 118, Nov. 1996, pp. 473-481 (10 pages).

Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).

Charman WN, "The Eye in Focus: Accommodation and Presbyopia," *Clinical and Experimental Optometry*, vol. 91, May 2008, pp. 207-225 (19 pages).

Cox CA, Krueger RR, "Monovision with Laser Vision Correction," *Ophthalmology Clinics of North Amermica*, vol. 19, No. 1, Mar. 2006, pp. 71-75 (7 pages).

Doss JD, Albillar JI, "A Technique for the Selective Heating of Corneal Stroma," *Contact & Intraocular Lens Medical Journal*, vol. 6, No. 1, Jan.- Mar. 1980, pp. 13-17 (8 pages).

Elsheikh A, Anderson K, "Comparative Study of Corneal Strip Extensometry and Inflation Tests," *Journal of the Royal Society Interface*, vol. 2, May 2005, pp. 177-185 (10 pages).

Evans BJW, "Monovision: a Review," *Ophthalmic and Physiological Optics*, vol. 27, Jan. 2007, pp. 417-439 (23 pages).

Gasset AR, Kaufman HE, "Thermokeratoplasty in the Treatment of Keratoconus," *American Journal of Ophthalmology*, vol. 79, Feb. 1975, pp. 226-232 (8 pages).

Gloster J, Perkins ES, "The Validity of the Imbert-Flick Law as Applied to Applanation Tonometry," *Experimental Eye Research*, vol. 2, Jul. 1963, pp. 274-283 (10 pages).

Gupta N, Naroo SA, "Factors Influencing Patient Choice of Refractive Surgery or Contact Lenses and Choice of Centre," *Contact Lens & Anterior Eye*, vol. 29, Mar. 2006, pp. 17-23 (7 pages).

Hamilton DR, Hardten DR, Lindstrom RL, "Thermal Keratoplasty," *Cornea*, 2$^{nd}$ Edition, Chapter 167, 2005, pp. 2033-2045 (13 pages).

Hersh PS, "Optics of Conductive Keratoplasty: Implication for Presbyopia Management," *Transactions of the American Ophthalmological Society*, vol. 103, 2005, pp. 412-456 (45 pages).

Hjortdal JO, "Extensibility of the Normo-Hydrated Human Cornea," *Acta Ophthalmologica Scandinavica*, vol. 73, No. 1, Feb. 1995, pp. 12-17 (7 pages).

Hori-Komai Y, Toda I, Asano-Kato N, Tsubota K, "Reasons for Not Performing Refractive Surgery," *Journal of Cataract & Refractive Surgery*, vol. 28, May 2002, pp. 795-797 (3 pages).

Illueca C, Alió JL, Mas D, Ortiz D, Pérez J, Espinosa J, Esperanza S, "Pseudoaccommodation and Visual Acuity with Technovision PresbyLASIK and a Theoretical Simulated Array® Multifocal Intraocular Lens," *Journal of Refractive Surgery*, vol. 24, Apr. 2008, pp. 344-349 (6 pages).

Jain S, Arora I, Azar DT, "Success of Monovision in Presbyopes: Review of the Literature and Potential Applications to Refractive Surgery," *Survey of Ophthalmology*, vol. 40, No. 6, May-Jun. 1996, pp. 491-499 (9 pages).

Tin GJC, Lyle A, Merkley KH, "Laser in Situ Keratomileusis for Primary Hyperopia," *Journal of Cataract & Refractive Surgery*, vol. 31, Apr. 2005, pp. 776-784 (9 pages).

Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).

Llovet F, Galal A, Benitez-del-Castillo J-M, Ortega J, Martin C, Baviera J, "One-Year Results of Excimer Laser in Situ Keratomileusis for Hyperopia," *Journal of Cataract & Refractive Surgery*, vol. 35, Jul. 2009, pp. 1156-1165 (10 pages).

Louie TM, Applegate D, Kuenne CB, Choi LJ, Horowitz DP, "Use of Market Segmentation to Identify Untapped Consumer Needs in Vision Correction Surgery for Future Growth," *Journal of Refractive Surgery*, vol. 19, No. 5, Sep.-Oct. 2003, pp. 566-576 (12 pages).

Maxwell WA, Lane SS, Zhou F, "Performance of Presbyopia-Correcting Intraocular Lenses in Distance Optical Bench Tests," *Journal of Cataract & Refractive Surgery*, vol. 35, Jan. 2009, pp. 166-171 (6 pages).

McDonald MB, Durrie D, Asbell P, Maloney R, Nichamin L, "Treatment of Presbyopia With Conductive Keratoplasty: Six-Month Results of the 1-Year United States FDA Clinical Trial," *Cornea*, vol. 23, No. 7, Oct. 2004, pp. 661-668 (8 pages).

McDonald MB, "Conductive Keratoplasty: a Radiofrequency-Based Technique for the Correction of Hyperopia," *Transactions of the American Ophthalmological Society*, vol. 103, Dec. 2005, pp. 512-536 (25 pages).

Moriera MD, Garbus JJ, Fasano A, Lee M, Clapham TN, McDonnel PJ, "Multifocal Corneal Topographic Changes With Excimer Laser Photorefractive Keratectomy," *Archives of Ophthalmology*, vol. 110, Jul. 1992, pp. 994-999 (6 pages).

Nash IS, Greene PR, Foster CS, "Comparison of Mechanical Properties of Keratoconus and Normal Corneas," *Experimental Eye Research*, vol. 35, 1982, pp. 413-424 (12 pages).

Newman JM, "Analysis, Interpretation, and Prescription for the Ametropias and Heterophorias," *Borish's Clinical Refraction*, 1998, pp. 776-822 (49 pages).

Pandolfi A, Manganiello F, "A Model for the Human Cornea: Formulation and Numerical Analysis," *Biomechanics and Modeling in Mechanobiology*, vol. 5, Jan. 2006, pp. 237-246 (10 pages).

Pertaub R, Ryan TP, "Numerical Model and Analysis of an Energy-Based System Using Microwaves for Vision Correction," *Proceedings of SPIE*, vol. 7181, Feb. 2009, p. 718105-1 to 718105-14 (14 pages).

Petroll WM, Roy P, Chuong CJ, Hall B, Cavanagh HD, Jester JV, "Measurement of Surgically Induced Corneal Deformations Using Three-Dimensional Confocal Microscopy," *Cornea*, vol. 15, No. 2, Mar. 1996, pp. 154-164 (12 pages).

Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," *Journal of Refractive Surgery*, vol. 24, May 2008, pp. 494-500 (7 pages).

Pinsky PM, Datye DV, "A Microstructurally-Based Finite Element Model of the Incised Human Cornea," *Journal of Biomechanics*, vol. 24, No. 10, Apr. 1991, pp. 907-922 (15 pages).

Pinsky PM, Datye DV, "Numerical Modeling of Radial, Astigmatic, and Hexagonal Keratotomy," *Refractive and Conical Surgery*, vol. 8, No. 2, Mar.-Apr. 1992, pp. 164-172 (11 pages).

Pinsky PM, van der Heide D, Chernyak D, "Computational Modeling of Mechanical Anisotropy in the Cornea and Sclera," *Journal of Cataract & Refractive Surgery*, vol. 31, Jan. 2005, pp. 136-145 (10 pages).

Riley C, Chalmers RL, "Survey of Contact Lens-Wearing Habits and Attitudes Toward Methods of Refractive Correction: 2002 Versus 2004," *Optometry and Vision Science*, vol. 82, No. 6, Jun. 2005, pp. 555-561 (7 pages).

Rosenbloom A, "New Aged and Old Aged: Impact of the Baby Boomer," *Journal of the American Optometry Association*, vol. 74, No. 4, Apr. 2003, pp. 211-213 (5 pages).

Rutzen AR, Roberts CW, Driller J, Gomez D, Lucas BC, Lizzi FL, Coleman DJ., "Production of Corneal Lesions Using High-Intensity Focused Ultrasound," *Cornea*, vol. 9, No. 4, Oct. 1990, pp. 324-330 (8 pages).

Ryan TP, Pertaub R, Meyers SR, Dresher RP, Scharf R., "Experimental Results of a New System Using Microwaves for Vision Correction," *Proceedings of SPIE*, vol. 7181, Feb. 2009, pp. 718106.1 to 718106.17 (17 pages).

Seiler T, Matallana M, Bende T, "Laser Thermokeratoplasty by Means of a Pulsed Holmium: YAG Laser for Hyperopic Correction," *Refractive and Corneal Surgery*, vol. 6, No. 5, Sep.-Oct. 1990, pp. 335-339 (6 pages).

Seiler T, Matallana M, Sendler S, Bende T, "Does Bowman's Layer Determine the Biomechanical Properties of the Cornea?" *Refractive and Conical Surgery*, vol. 8, No. 2, Mar.-Apr. 1992, pp. 139-142 (6 pages).

Shin TJ, Vito RP, Johnson LW, McCarey BE, "The Distribution of Strain in the Human Cornea," *Journal of Biomechanics*, vol. 30, No. 5, May 1997, pp. 497-503 (7 pages).

Solomon KD, Fernandez de Castro LE, Sandoval HP, Biber JM, Groat B, Neff KD, Ying MS, French JW, Donnenfeld ED, Lindstrom RL, "LASIK World Literature Review: Quality of Life and Patient Satisfaction," *Ophthalmology*, vol. 116, No. 4, Apr. 2009, pp. 691-701 (11 pages).

Stanley PF, Tanzer DJ, Schallhorn SC, "Laser Refractive Surgery in the United States Navy," *Current Opinion Ophthalmology*, vol. 19, Jul. 2008, pp. 321-324 (4 pages).

Strenk SA, Strenk LM, Koretz JF, "The Mechanism of Presbyopia," *Progress in Retinal Eye Research*, vol. 24, May 2005, pp. 379-393 (15 pages).

Stringer H, Parr J., "Shrinkage Temperature of Eye Collagen," *Nature*, Dec. 1964, p. 1307 (1 page).

Sutton G., Patmore A.L., Joussen A.M., Marshall J., "Mannose 6-Phosphate Reduces Haze Following Excimer Laser Photorefractive Keratectomy," *Lasers and Light*, vol. 7, No. 2/3, 1996, pp. 117-119 (3 pages).

Telandro A., "Pseudo-Accommodation Cornea: a New Concept for Correction of Presbyopia," *Journal of Refractive Surgery*, vol. 20, No. 5, Sep.-Oct. 2004, pp. S714-S717 (5 pages).

Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).

Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).

Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).

Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-1111 (7 pages).

Wang JQ, Zeng YJ, Li XY, "Influence of Some Operational Variables on the Radial Keratotomy Operation," *British Journal of Ophthalmology*, vol. 84, Jan. 2000, pp. 651-6533 (4 pages).

Wollensak, G., et al., "Riboflavin/Ultraviolet-A-Induced Collagen Crosslinking for the Treatment of Keratoconus," *American Journal of Ophthalmology*, Ophthalmic Publ., Chicago, IL, US, vol. 135, No. 5, May 1, 2003, pp. 620-627 (8 pages).

Zelichowska B, Rękas M, Stankiewicz A, Cervino A, Montés-Micó R., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).

Chandonnet, CO2 Laser Annular Thermokeratoplasty: A Preliminary Study, Lasers in Surgery and Medicine 12:264-273 (1992), Wiley-Lill, Inc.

Muller et al., Br. J. Opthalmol 2001; 85:437-443 (April).

Naoumidi et al., J. Cataract Refract Surg. May 2006; 32(5):732-41.

Pallikaris et al., J. Cataract Refract Surg. Aug. 2005; 31(8):1520-29.

Acosta et al., Cornea. Aug. 2006;25(7):830-8.

Berjano et al.; "Radio-Fequency Heatng of the Conea: Theoretical Model and In Vitro Experiments"; IEEE Transactions on Biomedical Engineering; vol. 49; No. 3; Mar. 2002; pp. 196-205.

Berjano et. al.; "Ring Electrode for Radio-Frequency Heating of the Cornea: Modelling and In Vitro Experiments"; Medical & Biological Engineering & Computing 2003; vol. 41; pp. 630-639.

International Search Report mailed Aug. 14, 2009 for PCT/US2009/042204, (5 pages).

International Search Report mailed Nov. 20, 2009 for PCT/2009/059061 (3 pages).

International Search Report mailed Nov. 6, 2009 for PCT/US2009/057481 (2 pages).

International Search Report for PCT/US2010/029806 dated Jun. 1, 2010 (3 pages).

Written Opinion for PCT/US2010/029806 dated Jun. 1, 2010 (6 pages).

International Search Report for PCT/US2010/029791 dated Jun. 1, 2010 (3 pages).

Written Opinion for PCT/US2010/029791 dated Jun. 1, 2010 (6 pages).

Trembly et al.; Microwave Thermal Keratoplasty for Myopia: Keratoscopic Evaluation in Procine Eyes; Journal of Refractive Surgery; vol. 17; Nov./Dec. 2001; (8 pages).

* cited by examiner

SYSTEM AND METHOD FOR STABILIZING CORNEAL TISSUE AFTER TREATMENT

CROSS-REFERENCE TO RELATED APPLICATIONS

This application claims the benefit of U.S. Provisional Patent Application No. 61/256,714, which was filed on Oct. 30, 2009, the contents of which are entirely incorporated herein by reference.

BACKGROUND OF THE INVENTION

1. Field of the Invention

The invention pertains to the field of keratoplasty and, more particularly, to systems and methods for stabilizing corneal tissue after treatment of the corneal tissue.

2. Description of Related Art

A variety of eye disorders, such as myopia, hyperopia, astigmatism, and keratoconus involve abnormal shaping of the cornea. Keratoplasty reshapes the cornea to correct such disorders. For example, with myopia, the shape of the cornea causes the refractive power of an eye to be excessive. Parallel rays of light are focused in front of the retina, producing a blurred image of objects at a distance. Flattening aspects of the cornea's shape about the visual axis through keratoplasty decreases the refractive power of an eye with myopia and causes the image to be properly focused at the retina.

In another example, with hyperopia, the shape of the cornea causes the refractive power of an eye to be insufficient. Parallel rays of light are focused behind the retina, producing a blurred image of objects proximate to the eye. Steepening or bulging aspects of the cornea's shape about the visual axis through keratoplasty, such as by removing a ring of tissue from the outer edge of the cornea, increases the refractive power of the eye, and causes the image to be properly focused at the retina.

With astigmatism and keratoconus, the surface of the cornea or the lens behind the cornea is not spherically shaped, and is instead shaped irregularly. An astigmatic eye is often shaped like the back of a spoon, causing parallel rays of light to focus at two separate points, creating a distorted image, and can accompany hyperopia or myopia. A keratoconus eye has more of a conical shape than a normal, gradual curve. In order to cause the image to be properly focused at the retina, the cornea can be given an overall more spherical shape using keratoplasty. For example, with respect to keratoconus, the abnormally steep curves in the cornea can be flattened.

Invasive surgical procedures, such as laser-assisted in-situ keratomileusis (LASIK), may be employed to reshape the cornea. However, such surgical procedures may typically require an extended healing period after surgery. Furthermore, such surgical procedures may involve complications caused by the cutting of a flap in the cornea to provide access to the stromal layer, such as dry eye syndrome caused by the severing of corneal nerves.

Many other serious, risky complications may arise in LASIK due to the cutting of the flap, such as striae, ectasia, buttonhole flap, and free flap. For example, striae, or wrinkles in the corneal flap, can occur following surgery due to the improper replacement of the flap during surgery and/or movement of the flap caused by normal activity post-surgery. Although it does not require correction in some cases, in others surgical correction is necessary to re-lift and smooth the flap.

In ectasia, the corneal flap is cut too deep and/or too much tissue is removed, causing the remaining corneal tissue can become too thin. The thinness of corneal tissue can cause it to weaken under normal, everyday pressure, causing it to bulge or deform. Such deformation can itself cause residual myopia and astigmatism that may require contact lenses to be worn despite the LASIK surgery. In severe cases, a corneal transplant may be necessary.

Buttonhole flap can also result from corneal flap cutting, which refers to a tear, uneven cut or rip in the flap. This can be caused by a variety of factors, including improper placement of the blade, the use of an excessively worn blade, or the use of an improperly sized blade. In other cases, the flap rips when it is placed back over the eye at the end of surgery. This can result in astigmatism and scarring that can worsen vision beyond its original state, and requires surgical correction once the flap has time to heal, usually around 6 months post-op.

Free flap is caused by the complete removal of the corneal flap. In other words, no connecting hinge is maintained between the flap and the eye. This can be caused by a loss of suction at the blade as it is creating the flap or by operator error. In some cases, the surgery can be completed as usual and the flap replaced without the hinge. However, this may increase the risk of other flap complications such as striae or buttonhole flap resulting from the increased handling required to remove and replace the flap without a hinge. In addition, the flap can suffer irreparable harm or be lost entirely, requiring that a corneal transplant be performed on the patient.

Thermokeratoplasty, on the other hand, is a noninvasive procedure that eliminates the need to cut a flap in the eye to correct corneal abnormalities. Thermokeratoplasty may be used to correct the vision of persons who have disorders associated with abnormal shaping of the cornea, such as myopia, hyperopia, astigmatism, and keratoconus, as described above. Thermokeratoplasty may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of heat energy according to particular patterns, including, but not limited to, circular or annular patterns, may cause aspects of the cornea to flatten and improve vision in the eye, without resorting to surgical intervention.

SUMMARY OF THE INVENTION

Embodiments according to aspects of the present invention provide systems and methods for stabilizing corneal tissue after treatment of the corneal tissue. For example, thermokeratoplasty may be applied to the corneal tissue to address disorders associated with abnormal shaping of the cornea. To stabilize the desired structural changes caused by the treatment, embodiments apply ophthalmic formulations that help to inhibit wound healing. Wound healing may occur in response to the application of the treatment and may produce further structural changes that mitigate or alter the desired effects of the treatment.

In some embodiments, the ophthalmic formulation applied to help inhibit wound healing may include Interleukin 10 (IL-10). IL-10, also referred to as human cytokine synthesis inhibitory factor (CSIF), is an anti-inflammatory cytokine that enhances antibody responses within humans. As recognized by one skilled in the art, cytokine consists of small, cell-signaling protein molecules that are produced by cells of the nervous and immune systems. IL-10 is in the four-α-helix bundle family, meaning that it has a three-dimension structure with four bundles of α-helices.

In other embodiments, the ophthalmic formulation may include Transforming Growth Factor beta 3 (TGFb3). TGFb3 is a protein produced by platelets, macrophages and fibroblasts that regulates the healing process in humans. TGFb3 often interacts, or binds together, with the Transforming Growth Factor beta receptor 2 (TGFbr2), a single-pass receptor and tumor suppressor gene. In further embodiments, the ophthalmic formulation may include Mannose 6-phosphate (M6P). M6P is a molecule bound by lectin in the immune system, and is expressed by the molecular formula $C_6H_{13}O_9P$.

It is understood, however, that embodiments of the present invention are not limited to the use of IL-10, TGFb3, or M6P. In general, embodiments of the present invention can apply any drug that inhibits healing pathways to prevent wound healing after treatment of the eye, e.g., thermally induced shape change in the cornea.

According to one embodiment of the invention, a method for applying therapy to an eye is described. The method comprises the steps of positioning an electrical energy conducting element in contact with a surface of an eye; applying electrical energy to an area of the eye with the electrical energy conducting element, the electrical energy reshaping the area of the eye to a new shape, the new shape being determined by a pattern of energy application; and applying a wound healing inhibitor to the surface of the eye, the wound healing inhibitor reducing at least one of corneal haze and central islands of the eye.

In another embodiment of the invention, a system for applying therapy to an eye is described. The system comprises an electrical energy source; an electrical energy conducting element in contact with the electrical energy source, the electrical energy conducting element having a proximal end configured to receive electrical energy generated by the electrical energy source, and a distal end configured to apply electrical energy; a wound healing inhibitor configured to reduce at least one of corneal haze and central islands of an eye; and a wound healing inhibitor delivery element in contact with the wound healing inhibitor.

These and other aspects of the present invention will become more apparent from the following detailed description of the preferred embodiments of the present invention when viewed in conjunction with the accompanying drawings.

DETAILED DESCRIPTION

Figure 1:
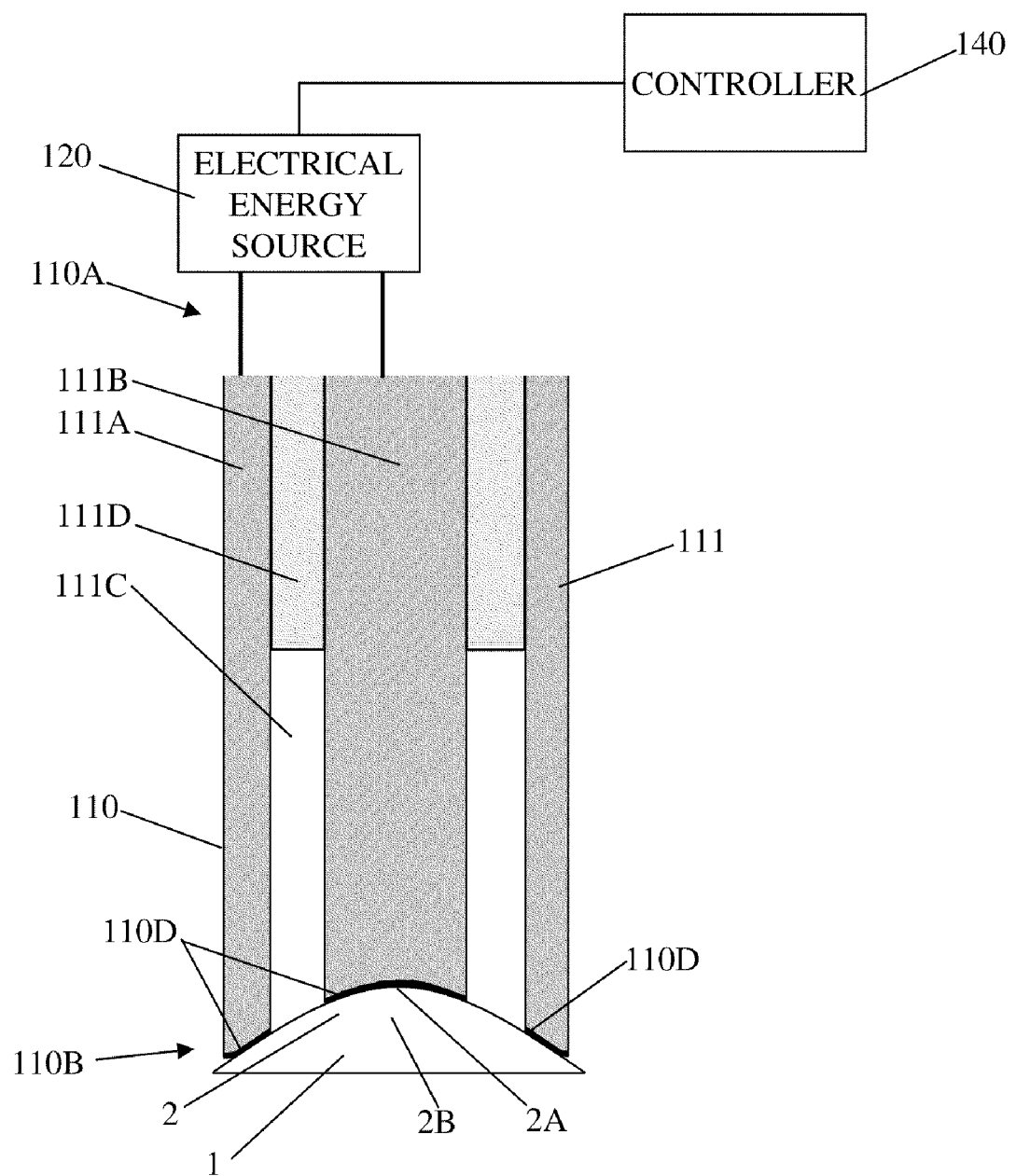
FIG. 1 illustrates an example system for applying heat to a cornea of an eye to cause reshaping of the cornea.

FIG. 1 illustrates an example system for applying energy to a cornea 2 of an eye 1 to generate heat and cause reshaping of the cornea. In particular, FIG. 1 shows an applicator 110 with an electrical energy conducting element 111 that is operably connected to an electrical energy source 120, for example, via conventional conducting cables. The electrical energy conducting element 111 extends from a proximal end 110A to a distal end 110B of the applicator 110. The electrical energy conducting element 111 conducts electrical energy from the source 120 to the distal end 110B to apply energy to the cornea 2, which is positioned at the distal end 110B. In particular, the electrical energy source 120 may include a microwave oscillator for generating microwave energy. For example, the oscillator may operate at a microwave frequency range of 400 MHz to 3000 MHz, and more specifically at a frequency of around 915 MHz or 2450 MHz. As used herein, the term "microwave" may correspond to a frequency range from about 10 MHz to about 10 GHz.

As further illustrated in FIG. 1, the electrical energy conducting element 111 may include two microwave conductors, or electrodes, 111A and 111B, which extend from the proximal end 110A to the distal end 110B of the applicator 110. In particular, the conductor 111A may be a substantially cylindrical outer conductor, while the conductor 111B may be a substantially cylindrical inner conductor that extends through an inner passage extending through the outer conductor 111A. With the inner passage, the conductor 111A may have a substantially tubular shape. The outer conductor 111A and inner conductor 111B may be formed, for example, of aluminum, stainless steel, brass, copper, other metals, coated metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 110A, the electrical energy generated by the electrical energy source 120, and directs microwave energy to the distal end 110B, where the cornea 2 is positioned.

The outer diameter of the inner conductor 111B is preferably larger than the pupil. In general, the outer diameter of the inner conductor 111B may be selected to achieve an appropriate change in corneal shape, i.e., keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of heat by the applicator 110.

A controller 140 may be employed to selectively apply the energy any number of times according to any predetermined or calculated sequence. The controller 140 may include a computer device to control the application of energy according to instructions provided via a computer-readable storage medium. In addition, the controller 140 may include a monitor and keyboard, or other user interface devices for receiving instructions from an operator.

Depending on the instructions, the energy may be applied for any length of time. Furthermore, the magnitude of energy being applied may also be varied. Adjusting such parameters for the application of energy determines the extent of changes that are brought about within the cornea 2. The system attempts to limit the changes in the cornea 2 to an appropriate amount of shrinkage of collagen fibrils in a selected region. When employing microwave energy to generate heat in the cornea 2, for example with the applicator 110, the microwave energy may be applied with low power (of the order of 40 W) and in long pulse lengths (of the order of one second). However, other systems may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may be coated with a material that can function both as an electrical insulator as well as a thermal conductor. A dielectric layer 110D may be employed along the distal end 110B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material deposited to a thickness of about 51 μm (0.002 inches). In general, an interposing layer, such as the dielectric layer 110D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired heating pattern in the cornea 2. The dielectric material may be elastic, such as polyurethane and silastic, or nonelastic, such as Teflon® and polyimides. The dielectric material may have a fixed dielectric constant or varying dielectric constant by mixing materials or doping the sheet, the variable dielectric being spatially distributed so that it may affect the microwave hearing pattern in a customized way. The thermal conductivity of the material may have fixed thermal properties (thermal conductivity or specific heat), or may also vary spatially, through mixing of materials or doping, and thus provide a means to alter the heating pattern in a prescribed manner. Another approach for spatially changing the heating pattern is to make the dielectric sheet material of variable thickness. The thicker region will heat less than the thinner region and provides a further means of spatial distribution of microwave heating.

The system of FIG. 1 is provided for illustrative purposes only, and other systems may be employed to apply energy to cause reshaping of the cornea. Other systems are described, for example, in U.S. patent application Ser. No. 12/208,963, filed Sep. 11, 2008, which is a continuation-in-part application of U.S. patent application Ser. No. 11/898,189, filed on Sep. 10, 2007, the contents of these applications being entirely incorporated herein by reference.

As described in U.S. patent application Ser. No. 12/208, 963, a cooling system may be employed in combination with the applicator 110 to apply coolant to the cornea 2 and determine how the energy is applied to the cornea 2. For example, the applicator 110 may include, internally or externally, at least one coolant delivery element in fluid communication with a coolant supply, or reservoir. The coolant delivery element delivers a coolant, or cryogen, from the coolant supply to the distal end of the applicator. In some embodiments, the coolant may be applied more directly to the dielectric layer 110D disposed along the distal end 110B, if the dielectric layer 110D substantially encloses the distal end 110B of the applicator 110. In general, the applicator may be employed to apply coolant to selectively cool the surface 2A of the cornea 2 positioned at the distal end 110B. The delivery of coolant from the coolant delivery element toward the corneal surface 2A, in sequence with the application of heat to the cornea 2, permits the corneal temperature to be increased to cause appropriate shrinkage of the collagen fibers in the targeted mid-depth region 2B and reshape the cornea 2, while also minimizing injury to the outer layer 2A, i.e. the epithelium, of the cornea 2.

In operation, the distal end 110B of the applicator 110 as shown in FIG. 1 is positioned on or near the corneal surface 2A. Preferably, the applicator 110 makes direct contact with the corneal surface 2A. In particular, such direct contact positions the conductors 111A and 111B at the corneal surface 2A, though a thin interposing dielectric layer 110D may be disposed between the conductors 111A and 111B and the corneal surface 2A. Accordingly, direct contact helps ensure that the pattern of microwave heating in the corneal tissue has substantially the same shape and dimension as the gap 111C between the two microwave conductors 111A and 111B.

Prior to positioning of the applicator 110 in contact with the corneal surface 2A, the corneal surface 2A may be scanned to make a topographical map showing the shape and curvature of the surface of the cornea. Then, with the conductors 111A and 111B positioned flush with the corneal surface 2A, the treatment may apply durations of microwave pulses to heat and reshape collagen and coolant pulses to protect the corneal surface. In one aspect, the treatment attempts to shrink the collagen in the cornea 2 and form a precisely controlled annular lesion in approximately the upper 150 μm of the stroma. The microwave treatment raises the temperature of an annulus, just below the surface of the cornea, to a temperature in the range of approximately 60 to 75° C. Using evaporative surface cooling techniques, the system cools the surface of the cornea during treatment to isolate and protect the epithelium and Bowman's membrane from microwave heating. Thus, the treatment is noninvasive, as there is no cutting or penetration of the eye. In one example application, the applicator 110 predictably flattens the central cornea to achieve mild-to-moderate myopic correction (−0.5 to −3.5 diopters, D) without compromising the biomechanical integrity of the cornea.

Accordingly, embodiments according to aspects of the present invention may use microwave energy emitted from the applicator 110, e.g., in a ring-shaped pattern, around the pupil to shrink stromal collagen and modify the dioptric power of the cornea, while a cooling system acts on the corneal surface to minimize thermal damage to the epithelium. In particular, electric field lines form a fringing pattern that extends into the corneal stroma to a depth determined by the applied power and applicator geometry. This electric field causes the polar water molecules to align themselves with the field; the rapid reversal of the sinusoidally-varying field causes frictional heating by these molecules as they rotate in place. This effect does not require a conduction current to flow through a point of electrical contact between a conductor and tissue; heating is caused by a displacement current.

Figure 2A:
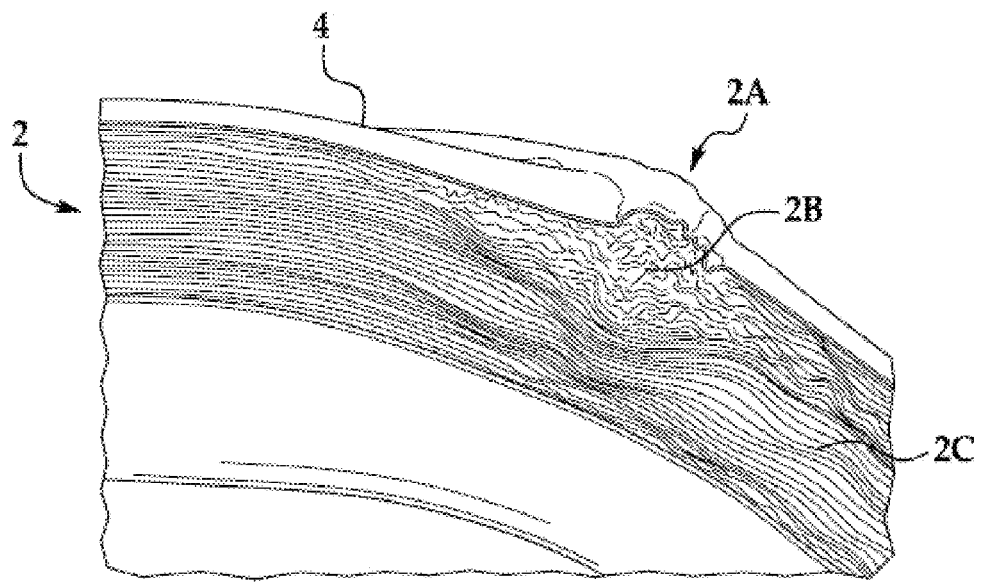
FIG. 2A illustrates a high resolution image of a cornea after heat has been applied.
Figure 2B:
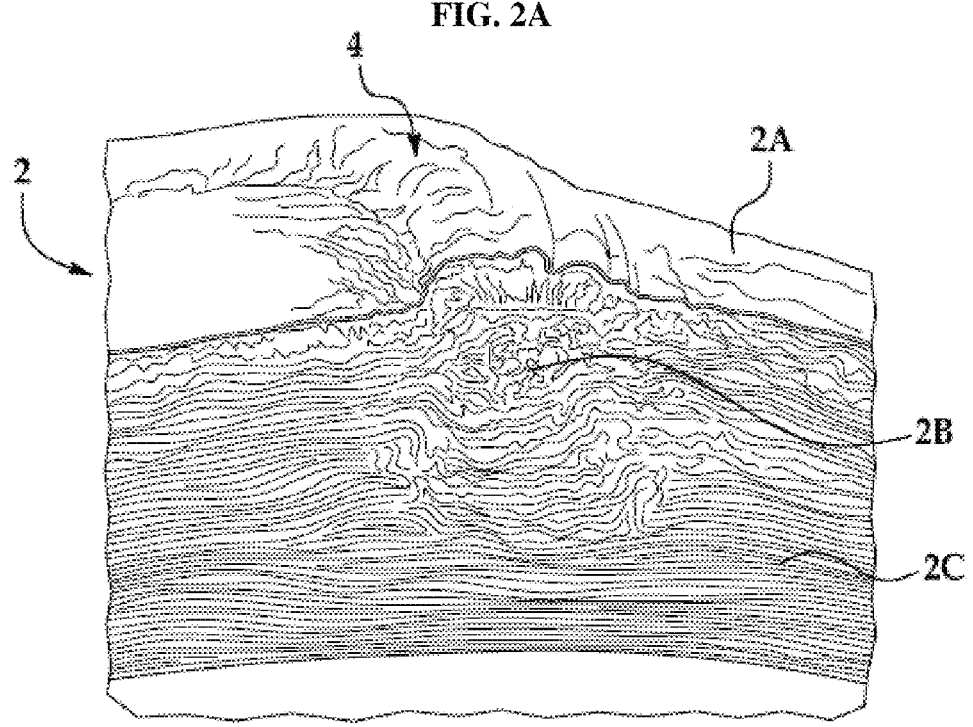
FIG. 2B illustrates another high resolution images of the cornea of FIG. 2A.

FIGS. 2A-D illustrate an example of the effect of applying heat to corneal tissue with a system for applying heat, such as the system illustrated in FIG. 1. In particular, FIGS. 2A and 2B illustrate high resolution images of cornea 2 after heat has been applied. As FIGS. 2A and 2B show, a lesion 4 extends from the corneal surface 2A to a mid-depth region 2B in the corneal stroma 2C. The lesion 4 is the result of changes in corneal structure induced by the application of heat as described above. These changes in structure result in an overall reshaping of the cornea 2. It is noted that the application of heat, however, has not resulted in any heat-related damage to the corneal tissue.

Figure 2C:
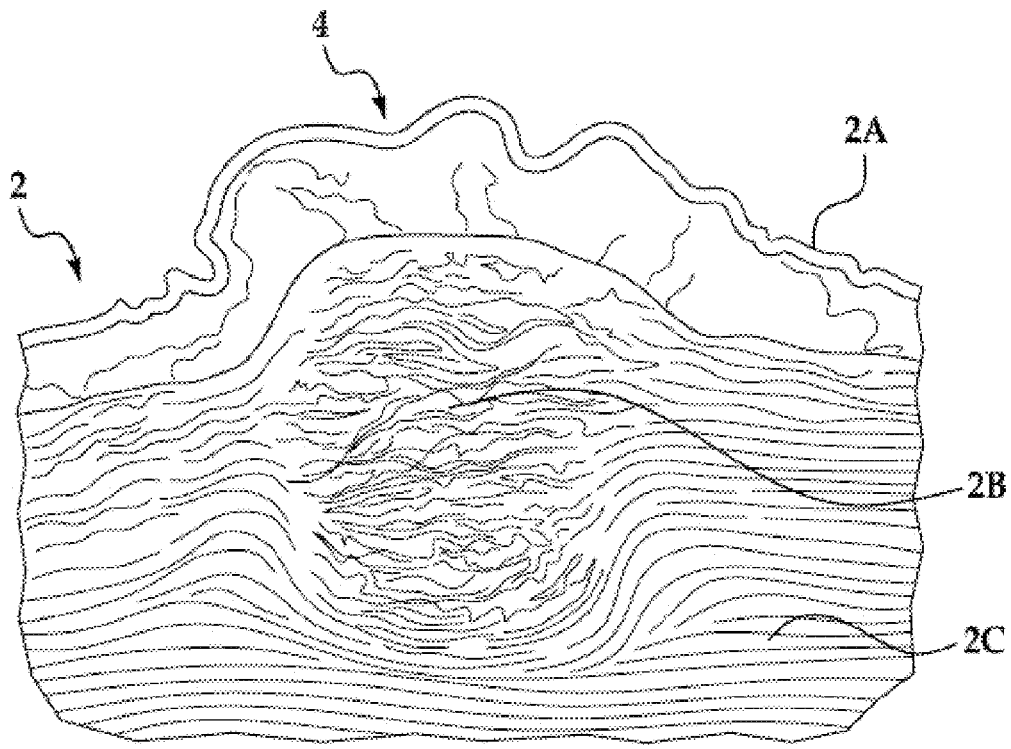
FIG. 2C illustrates a histology image of the cornea of FIG. 2A.
Figure 2D:
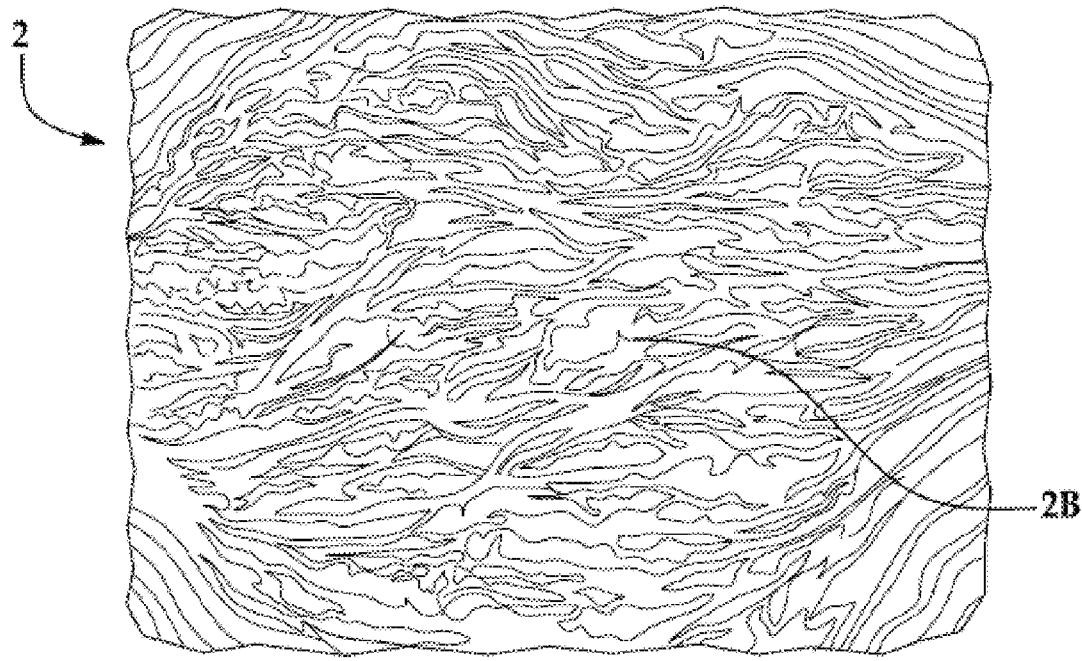
FIG. 2D illustrates another histology image of the cornea of FIG. 2A.

As further illustrated in FIGS. 2A and 2B, the changes in corneal structure are localized and limited to an area and a depth specifically determined by an applicator as described above. FIGS. 2C and 2D illustrate histology images in which the tissue shown in FIGS. 2A and 2B has been stained to highlight the structural changes induced by the heat. In particular, the difference between the structure of collagen fibrils in the mid-depth region 2B where heat has penetrated and the structure of collagen fibrils outside the region 2B is clearly visible. Thus, the collagen fibrils outside the region 2B remain generally unaffected by the application of heat, while the collagen fibrils inside the region 2B have been rearranged and formed new bonds to create completely different structures. In other words, unlike processes, such as orthokeratology, which compress areas of the cornea to reshape the cornea via mechanical deformation, the collagen fibrils in the region 2B are in an entirely new state.

In summary, energy is applied to a cornea through an applicator, such as the applicator 110 shown in FIG. 1, to generate heat that produces a desired reshaping of the cornea. Although the heat induces structural changes in the collagen fibrils of the cornea, the desired effects of reshaping the cornea may be mitigated or altered if the collagen fibrils continue to change after the desired reshaping has been achieved. In particular, further changes to the corneal structure may be caused by the wound healing response after the application of the energy to the cornea. The wound healing response may affect the final corneal shape and hence the refractive and visual outcome. In addition, the wound healing response may lead to the development of scar tissue having a lack of transparency, in addition to causing corneal haze and central islands. The degree to which the wound healing can be controlled determines whether the treatment actually yields the desired changes to the corneal shape.

Figure 3:
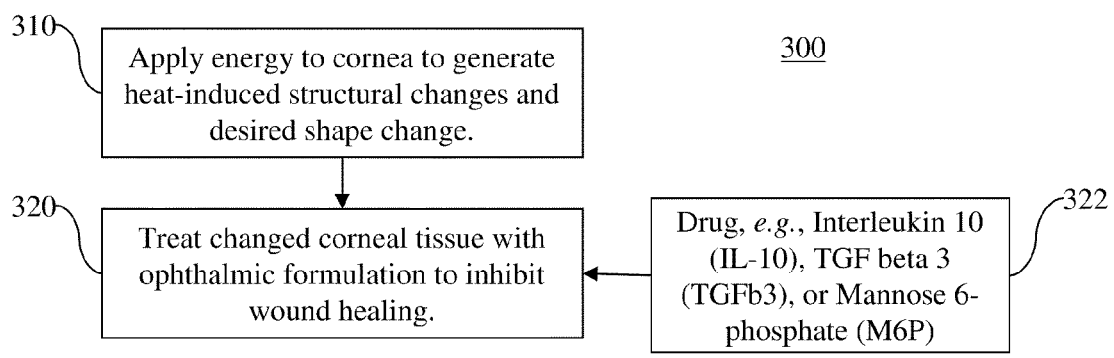
FIG. 3 illustrates an example application of a drug to inhibit wound healing according to aspects of the present invention.

Therefore, aspects of the present invention provide approaches for stabilizing the desired corneal structure and minimizing the effects of the wound healing that occur in response to the application of heat. Referring to FIG. 3, an example embodiment 300 according to aspects of the present invention is illustrated. Specifically, in step 310, energy is applied to corneal tissue to generate heat-induced structural changes and a desired shape change, as described previously. For example, the applicator 110 of FIG. 1 may be used to treat the cornea.

In step 320, a wound healing inhibitor comprising an ophthalmic formulation is applied to the cornea to inhibit the wound healing. Inhibited wound healing may be exhibited by, for example, reduced or prevented corneal haze, central islands, and a lack of transparency in the eye, that may otherwise be caused without the application of the inhibitor. The wound healing inhibitor can be applied by, for example, an eye dropper or a drug application device, such as a bandage, that is removably attached to the eye. The ophthalmic formulation includes a drug 322, which in some embodiments, may include Interleukin 10 (IL-10). In other embodiments, the drug 322 may include Transforming Growth Factor beta 3 (TGFb3), which may be recombinant or genetically engineered.

In another embodiment, the drug 322 may include Mannose 6-phosphate (M6P). The effects of M6P on corneal wound healing in rabbits following excimer laser photorefractive keratectomy (PRK) is described in G. Sutton, et al., Mannose 6-phosphate reduces haze following excimer laser photorefractive keratectomy, Lasers and Light, Vol. 7, No. 2/3, pp. 117-119 (1996), the contents of which are incorporated entirely herein by reference. In this study, a group of rabbits were exposed to identical excimer laser photorefractice keratectomy ablations and were treated with either a control drop of an M6P drop. A significant reduction in corneal haze was observed at 4 weeks in the M6P group compared to the control group. In addition, the M6P group had less subepithelial collagen. It is theorized that M6P acts by competing with latent Transforming Growth Factor beta (TGFb) at the Insulin Like Growth Factor II receptor. Although there are a number of growth factors which may affect the healing process, TGFb plays a key role. More specifically, TGFb2 of epithelial origin has been shown to be an inhibitor of stromal collegenase, which implies epithelial modulation of the underlying stromal wound healing. Indeed, neutralizing antibodies to TGFb can be used to modify wound healing. Thus, aspects of the present invention may apply drugs that control wound healing by determining TGFb activity. For example, a processor may be used to determine Transforming Growth Factor beta (TGFb) activity. In addition, the wound inhibitor delivery element can be adjusted based on the Transforming Growth Factor beta (TGFb) activity.

It is understood that embodiments of the present invention are not limited to the use of IL-10, TGFb3, or M6P. In general, embodiments of the present invention can apply any drug that inhibits healing pathways to prevent wound healing after treatment of the eye, such as treatment that thermally induces shape change in the cornea.

While the present invention has been described in connection with a number of exemplary embodiments, and implementations, the present inventions are not so limited, but rather cover various modifications, and equivalent arrangements. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with the spirit the invention reflected by the claims herein. Accordingly, the drawings and descriptions are to be regarded as illustrative in nature, and not as restrictive.

What is claimed is:

1. A system for applying therapy to an eye, the system comprising:
   an electrical energy source;
   an electrical energy conducting element in contact with the electrical energy source, the electrical energy conducting element having a proximal end configured to receive electrical energy generated by the electrical energy source, and a distal end configured to apply electrical energy;

a wound healing inhibitor including Mannose 6-phosphate (M6P), the wound healing inhibitor being configured to reduce corneal haze by competing with latent Transforming Growth Factor beta (TGFb) at an Insulin Like Growth Factor II receptor;

a wound healing inhibitor delivery element in contact with the wound healing inhibitor;

a processor configured to determine Transforming Growth Factor beta (TGFb) activity, a coolant supply; and a coolant delivery element in contact with the coolant supply, the coolant delivery element configured to deliver a pulse of coolant wherein the wound healing inhibitor delivery element is adjusted based on the Transforming Growth Factor beta (TGFb) activity.

2. The system according to claim 1, wherein the wound healing inhibitor delivery element is at least one of an eye dropper and a drug application device configured to be removably attached to the eye.

3. The system according to claim 1, wherein the electrical energy is microwave energy.

4. A system for applying therapy to an eye, the system comprising:

an electrical energy source;

an electrical energy conducting element in contact with the electrical energy source, the electrical energy conducting element having a proximal end configured to receive electrical energy generated by the electrical energy source, and a distal end configured to apply electrical energy;

a wound healing inhibitor delivery element including a wound healing inhibitor, the wound healing inhibitor including Mannose 6-phosphate (M6P); and a processor configured to determine Transforming Growth Factor beta (TGFb) activity, wherein the wound healing inhibitor delivery element is adjusted based on the Transforming Growth Factor beta (TGFb) activity.

5. The system according to claim 4, wherein the wound healing inhibitor delivery element is at least one of an eye dropper and a drug application device configured to be removably attached to the eye.

6. The system according to claim 4, wherein the electrical energy is microwave energy.

* * * * *